United States Patent [19]

Kemp, Jr. et al.

[11] Patent Number: 4,783,214

[45] Date of Patent: Nov. 8, 1988

[54] LOW OXYGEN CONTENT FINE SHPERICAL PARTICLES AND PROCESS FOR PRODUCING SAME BY FLUID ENERGY MILLING AND HIGH TEMPERATURE PROCESSING

[75] Inventors: Preston B. Kemp, Jr., Athens; Walter A. Johnson, Towanda, both of Pa.

[73] Assignee: GTE Products Corporation, Stamford, Conn.

[21] Appl. No.: 161,535

[22] Filed: Feb. 29, 1988

[51] Int. Cl.$^4$ ................................................. B22F 9/04
[52] U.S. Cl. ........................... 75/0.5 B; 75/0.5 BB; 75/0.5 BC; 75/251; 75/252
[58] Field of Search ........... 75/0.5 B, 0.5 BB, 0.5 BA, 75/0.5 R, 0.5 C

[56] References Cited

U.S. PATENT DOCUMENTS

| | | | |
|---|---|---|---|
| 3,909,241 | 9/1975 | Cheney et al. | 75/0.5 BB |
| 3,974,245 | 8/1976 | Cheney et al. | 75/0.5 BB |
| 4,264,354 | 4/1981 | Cheetham | 75/0.5 B |
| 4,711,660 | 12/1987 | Kemp, Jr. et al. | 75/251 |
| 4,711,661 | 12/1987 | Kemp, Jr. et al. | 75/251 |

*Primary Examiner*—Wayland Stallard

*Attorney, Agent, or Firm*—Donald R. Castle; L. Rita Quatrini

[57] ABSTRACT

A powder material and a process for producing the material are disclosed. The powder material consists essentially of spherical particles selected from the group consisting of metals, metal alloys, ceramic glasses, crystalline ceramic materials, and combinations thereof. The material is essentially free of elliptical shaped material and elongated particles having rounded ends. The material has a particle size of less than about 20 micrometers in diameter and has an oxygen content of less than about 0.8% by weight. The process for making the spherical particles involves reducing the size of a starting material to produce a finer powder essentially all of which has a particle size of less than about 20 micrometers in diameter. This is done by fluid energy milling. The finer powder is entrained in a carrier gas and passed through a high temperature zone at a temperature above the melting point of the powder, the temperature being from about 5500° C. to about 17,000° C. and created by a plasma jet, to melt at least about 50% by weight of the powder and form spherical particles of the melted portion. The powder is then rapidly and directly solidified while in flight. The carbon content of the particles is no greater than that of the starting material.

12 Claims, No Drawings

LOW OXYGEN CONTENT FINE SHPERICAL PARTICLES AND PROCESS FOR PRODUCING SAME BY FLUID ENERGY MILLING AND HIGH TEMPERATURE PROCESSING

CROSS REFERENCE TO RELATED APPLICATIONS

This invention is related to "Low Oxygen Content Fine Spherical Iron Based And Chromium Based Powder Particles and Producing Same by Fluid Energy Milling and High Temperature Processing".

This invention relates to fine spherical powder particles and to the process for producing the particles which involves mechanically reducing the size of a starting material by fluid energy or jet milling following by high temperature processing to produce fine spherical particles having oxygen contents of less than about 0.8% by weight. More particularly the high temperature process is a plasma process.

BACKGROUND OF THE INVENTION

U.S. Pat. Nos. 3,909,241 and 3,974,245 to Cheney et al relates to free flowing powders which are produced by feeding agglomerates through a high temperature plasma reactor to cause at least partial melting of the particles and collecting the particles in a cooling chamber containing a protective gaseous atmosphere where the particles are solidified.

U.S. Pat. No. 4,264,354 to Cheetham relates to producing spherical dental alloy powders by high frequency induction coil heating followed by cooling in a liquid medium.

Fine spherical metal particles are useful in applications such as filters, precision press and sinter parts, and injection molded parts.

Some of the better known processes for producing such metal powder particles are by gas or water atomization. Only a small percentage of the powder produced by atomization is less than about 20 micrometers. Therefore, yields are low and metal powder costs are high as a result and in the case of water atomization, the powder is often not spherical.

In European patent application No. WO8402864 published Aug. 2, 1984, there is disclosed a process for making ultra-fine powder by directing a stream of molten droplets at a repellent surface whereby the droplets are broken up and repelled and thereafter solidified as described therein. While there is a tendency for spherical particles to be formed after rebounding, it is stated that the molten portion may form elliptical shaped or elongated particles with rounded ends.

U.S. Pat. Nos. 4,711,660 and 4,711,661 relate to spherical particles and process for producing same by reducing the particle size of the material and high temperature processing followed by rapid solidification. The oxygen content of the spherical particles when the material is reduced in size by the preferred attritor milling is greater than about 0.8% by weight. It is desirable that the oxygen content be lower than this value for better sintering and better mechanical properties, etc.

SUMMARY OF THE INVENTION

In accordance with one aspect of this invention there is provided a powder material which consists essentially of spherical particles selected from the group consisting of metals, metal alloys, ceramic glasses, crystalline ceramic materials, and combinations thereof. The material is essentially free of elliptical shaped material and elongated particles having rounded ends. The materials has a particle size of less than about 20 micrometers in diameter and has an oxygen content of less than about 0.8% by weight.

In accordance with another aspect of this invention, there is provided a process for making the spherical particles which involves reducing the size of a starting material to produce a finer powder essentially all of which has a particle size of less than about 20 micrometers in diameter. This is done by fluid energy milling. The finer powder is entrained in a carrier gas and passed through a high temperature zone at a temperature above the melting point of the powder, the temperature being from about 5500° C. to about 17,000° C. and created by a plasma jet, to melt at least about 50% by weight of the powder and form spherical particles of the melted portion. The powder is then rapidly and directly solidified while in flight. The carbon content of the particles is no greater than that of the starting material.

DETAILED DESCRIPTION OF THE INVENTION

For a better understanding of the present invention, together with other and further objects, advantages and capabilities thereof, reference is made to the following disclosure and appended claims in connection with the above description of some of the aspects of the invention.

The starting material of this invention can be essentially any type of material. However, the preferred materials are metals, metal alloys, ceramic glasses, and crystalline ceramic materials and combinations of these. The major criteria for producing ceramic materials by this process is that they maintain chemical stability up to their melting point.

The size of the starting material is first reduced to produce a finer powder material. The starting material can be of any size or diameter initially, since one of the objects of this invention is to reduce the diameter size of the material from the initial size. Essentially all of the material is reduced to a particle size of less than about 20 micrometers in diameter as measured by conventional techniques such as air or liquid settling, or laser diffractometry.

The size reduction is accomplished by a group of processes commonly called "jet milling" or "fluid energy milling", including fluidized bed opposed jet milling, the "Coldstream" process in which a stream of gas and the starting material are impinged against a fixed target, etc. All references made herein to "jet milling" or "fluid energy milling" are understood to refer to this group of processes. In the process of the invention, there are no moving parts except for gas compressors to produce the fluid energy stream. Energy is imparted to the particles by the fluid or gas that is, by the velocity of the fluid. All of these processes impart high velocities to the material which is being ground and impact the accelerated particles against each other or against a solid substrate at a sufficient force to shatter or break the particles into smaller fragments.

In U.S. Pat. Nos. 4,711,660 and 4,711,661 relate to particle size reduction followed by high temperature processing and rapid solidification to form spherical particles. These patents stress media/mechanical motion or vibration or reduce particle size. These patents relate to processes in which the size reduction is done in a liquid medium and the material must be dried before subsequent high temperature processing. Both of these steps increase the likelihood for oxidation of the powder. By contrast, according to this invention, the size reduction can be done with the material in the dry state in an inert atmosphere. Only the correct size powder is produced and therefore there is no need for screening or size classification before high temperature processing. Furthermore, the processes of these patents result in powders which have a carbon content exceeding that required in some applications. This is due to the fact that size reduction occurs typically in a liquid organic medium which breaks down or is trapped within the powder particles. This results in an increase in the carbon content of the powder. By contrast, the present invention is carried out with the material in the dry state and the carbon content is therefore not increased. Therefore, the present invention is more suitable for some alloy systems, for example, low carbon stainless steel powders. When fluid energy milling is used, the oxygen content in the resultant spherical powder particles is less than about 0.8% by weight, and the carbon content is essentially no greater than that of the starting material. Also the process operates at a higher efficiency than prior art methods of gas or water atomization or the processes of U.S. Pat. Nos. 4,711,660 and 4,711,661 because only the correct size powder is discharged from the jet milling apparatus to convert it to spherical particles by high temperature processing. The prior art methods of mechanical size reduction are batch processes. Therefore all material undergoes high temperature processing, even if a portion of it is not the correct size. Thus, more material must undergo the high temperature processing to yield a given amount of product, and more post-high temperature treatment classifying is necessary to yield the desired final size distribution. The process of this invention yields a more uniform size reduced material for subsequent high temperature processing than does prior art processing. This is so because the fluid energy milling is a continuous process. The oversize powder is recycled to the fluid energy milling process while the correct size material which is finer than the starting material is discharged from the mill for subsequent high temperature process. This is important because melting efficiency (the weight ratio of melted particles to total particles) is increased when the material that is subjected to the high temperature process is more uniform in size.

The preferred jet mill to accomplish size reduction is the fluidized bed opposed jet mill invented by Alpine. The mill is comprised of a cylindrical grinding chamber with an Alpine classifier mounted at the top. Compressed air, nitrogen, or inert gases is introduced into the mill through three or more horizontally oriented nozzles circumferentially spaced around the lower portion of the grinding chamber. Material is introduced into the chamber by a feeder at the bottom of the chamber or through a tube entering the grinding chamber above the gas jets. Because of the gas flowing into the mill, the material which is being size reduced forms a fluidized bed at the bottom of the grinding chamber. Gas leaves the nozzles at supersonic velocities and accelerates the material to be reduced in size. Particles of material are entrained in each gas jet and impact near the center of the grinding chamber with particles entrained in the other gas jets. Particles fracture and therefore, size reduction occurs at this stage of the process.

The mixture of size reduced and unground material travels upwards through the grinding chamber to the air classifier, which is a finned wheel (similar in appearance to a "squirrel cage" blower) rotating at a high speed (>5,000 rpm). The wheel rejects particles above a certain size (which is adjustable) and returns these unground or partially ground particles to the fluidized bed of the grinding chamber. The oversize material rejected by the classifier wheel is reentrained in the gas jets for further grinding. Fine particles of the desired size pass through the classifier wheel, where they are collected by conventional means, such as gas cyclones or filters. New starting material is fed into the mill at a rate equal to the rate at which fine size reduced powder leaves the mill.

If a metal or metal alloy powder is size reduced by the above described jet mill with nitrogen or an inert gas as the grinding/atmosphere gas, the oxygen content of the size reduced powder is only slightly greater than the starting oxygen content. No matter which gas is used for milling, contamination of the material other than by oxygen during size reduction is minimal, even compared to other jet milling processes, because the material impacts and fractures against itself. Wear of the jet milling apparatus, which implies contamination of the material which is being size reduced, is minimal. The above described equipment offers many advantages over conventional tumbling or stirred ball mills for the size reduction of metal powders. In conventional mills, milling is usually conducted in an organic solvent, which leads to carbon contamination. This does not happen in the process of the present invention. Also, the size reduced material must be dried before conversion to essentially spherical particles, and oxidation is nearly unavoidable.

The reduced size material is then entrained in a carrier gas such as argon and passed through a high temperature zone at a temperature above the melting point of the finer powder for a sufficient time to melt at least about 50% by weight of the finer powder and form essentially fine particles of the melted portion. Some additional particles can be partially melted or melted on the surface and these can be spherical particles in addition to the melted portion. The preferred high temperature zone is a plasma.

Details of the principles and operation of plasma reactors are well known. The plasma has a high temperature zone, but in cross section the temperature can vary typically from about 5500° C. to about 17,000° C. The outer edges are at low temperatures and the inner part is at a higher temperature. The retention time depends upon where the particles entrained in the carrier gas are injected into the nozzle of the plasma gun. Thus, if the particles are injected into the outer edge, the retention time must be longer, and if they are injected into the inner portion, the retention time is shorter. The residence time in the plasma flame can be controlled by choosing the point at which the particles are injected into the plasma. Residence time in the plasma is a function of the physical properties of the plasma gas and the powder material itself for a given set of plasma operating conditions and powder particles. Larger particles are more easily injected into the plasma while smaller particles tend to remain at the outer edge of the plasma jet or are deflected away from the plasma jet.

After the material passes through the plasma, it cools, and is rapidly solidified. Generally the major weight portion of the material is converted to spherical particles. Generally greater than about 75% and most typically greater than about 85% of the material is converted to spherical particles by the high temperature treatment. Nearly 100% conversion to spherical particles can be attained. The major portion of the spherical particles are less than about 20 micrometers in diameter. The particle size of the plasma treated particles is largely dependent of the size of the material obtained in the mechanical size reduction step. Most typically greater than about 99% of the particles are less than about 20 micrometers.

More preferred particle sizes are less than about 15 micrometers in diameter and most preferably less than about 10 micrometers in diameter, and it is preferred that the particles be greater than about 1 micrometer in diameter.

After cooling and subsequent resolidification, the resulting high temperature treated material can be classified to remove the major spheroidized particle portion from the essentially non-spheroidized minor portion of particles and to obtain the desired particle size distribution. The classification can be done by standard techniques such as screening or air classification.

The unmelted minor portion can then be reprocessed according to the invention to convert it to fine spherical particles.

The powder materials of this invention are essentially spherical particles which are essentially free of elliptical shaped material and essentially free of elongated particles having rounded ends. These characteristics can be present in the particles made by the process described in European Patent Application No. WO8402864 as previously mentioned.

Furthermore, the levels of chemical contamination (carbon, oxygen, etc.) in the final product of this invention are much lower than those found in the spherical particles made by prior art high temperature processes. The oxygen levels in the particles produced by the process of the present invention are typically less than about 0.8% by weight and more typically less than about 0.5% by weight with levels as low as about 0.25% by weight can be achieved.

Spherical particles have an advantage over non-spherical particles in injection molding and pressing and sintering operations. The lower surface area of spherical particles as opposed to non-spherical particles of comparable size, and the flowability of spherical particles makes spherical particles easier to mix with binders and easier to dewax.

While there has been shown and described what are at present considered the preferred embodiments of the invention, it will be obvious to those skilled in the art that various changes and modifications may be made therein without departing from the scope of the invention as defined by the appended claims.

What is claimed is:
1. A process comprising:
   (a) reducing the size of a starting material from which said powder is to be made by fluid energy milling to produce a finer powder, essentially all of which has a particle size of less than about 20 micrometers in diameter;
   (b) entraining said finer powder in a carrier gas and passing said powder through a high temperature zone at a temperature above the melting point of said finer powder, said temperature being from about 5500° C. to about 17,000° C., said temperature being created by a plasma jet to melt at least about 50% by weight of said finer powder to form essentially fine spherical particles of said melted portion; and
   (c) rapidly and directly resolidifying the resulting high temperature treated material while said material is in flight, to form fine spherical particles having a particle size of less than about 20 micrometers in diameter, said particles being essentially free of elliptical shaped material and essentially free of elongated particles having rounded ends, said particles having an oxygen content of less than about 0.8% by weight, and a carbon content of no greater than the carbon content of said starting material.

2. A process of claim 1 wherein the size of said starting material is reduced by fluidized bed opposed jet milling said material to produce said finer powder.

3. A process of claim 1 wherein after said resolidification, said high temperature treated material is classified to obtain the desired particle size of said spherical particles.

4. A process of claim 1 wherein said material is selected from the group consisting of metals, metal alloys, ceramic glasses, and crystalline ceramic glasses, and combinations thereof.

5. A process of claim 4 wherein said material is selected from the group consisting of metals and metal alloys.

6. A powder material consisting essentially of spherical particles selected from the group consisting of metals, metal alloys, ceramic glasses, and crystalline ceramic materials, and combinations thereof, said powder material being essentially free of elliptical shaped material and essentially free of elongated particles having rounded ends, said powder material having a particle size of less than about 20 micrometers in diameter, said powder material being made by jet milling a starting material followed high temperature processing and direct solidification of the resulting high temperature treated material, said powder material having an oxygen content of less than about 0.8% by weight and a carbon content of no greater than the carbon content of said starting material.

7. A powder material of claim 6 wherein said particles are selected from the group consisting of metals and metal alloys.

8. A powder material of claim 6, wherein the particle size of said spherical particles is less than about 15 micrometers in diameter.

9. A powder material of claim 6 wherein the particle size is less than about 10 micrometers in diameter.

10. A powder material of claim 6 wherein the particle size is greater than about 1 micrometer in diameter.

11. A powder material of claim 8 wherein the particle size is greater than about 1 micrometer in diameter.

12. A powder material of claim 9 wherein the particle size is greater than about 1 micrometer in diameter.

* * * * *